(12) United States Patent
Tellman

(10) Patent No.: US 12,213,712 B2
(45) Date of Patent: Feb. 4, 2025

(54) BONE IMPLANT HANDLING INSTRUMENT FOR PLACING A BONE IMPLANT IN AN OPERATIVE POSITION

(71) Applicant: TRIMED, INCORPORATED, Santa Clarita, CA (US)

(72) Inventor: Lukas Tellman, Falsterbo (SE)

(73) Assignee: TriMed Inc., Santa Clarita, CA (US)

( * ) Notice: Subject to any disclaimer, the term of this patent is extended or adjusted under 35 U.S.C. 154(b) by 441 days.

(21) Appl. No.: 17/738,536

(22) Filed: May 6, 2022

(65) Prior Publication Data
US 2022/0257292 A1 Aug. 18, 2022

Related U.S. Application Data

(63) Continuation-in-part of application No. 16/875,760, filed on May 15, 2020, now Pat. No. 11,324,539.

(60) Provisional application No. 62/848,018, filed on May 15, 2019.

(51) Int. Cl.
| | |
|---|---|
| *A61B 17/80* | (2006.01) |
| *A61B 17/00* | (2006.01) |
| *A61B 17/064* | (2006.01) |
| *A61B 17/10* | (2006.01) |
| *A61B 17/56* | (2006.01) |
| *A61B 17/88* | (2006.01) |
| *A61B 17/90* | (2006.01) |
| *A61F 2/46* | (2006.01) |

(52) U.S. Cl.
CPC ........ *A61B 17/808* (2013.01); *A61B 17/0642* (2013.01); *A61B 17/10* (2013.01); *A61B 17/809* (2013.01); *A61B 17/90* (2021.08)

(58) Field of Classification Search
CPC . A61B 17/808; A61B 17/809; A61B 17/0642; A61B 17/80; A61B 17/8004; A61B 17/8019; A61B 17/8061; A61B 17/8872; A61B 2017/0645; A61B 2017/564; A61F 2/46; A61F 2/4611; A61F 2/4603; A61F 2002/4622; A61F 2002/4625
USPC .................................. 606/297, 279, 99, 281
See application file for complete search history.

(56) References Cited

U.S. PATENT DOCUMENTS

| | | | | |
|---|---|---|---|---|
| 8,821,508 | B2 * | 9/2014 | Medoff | A61B 17/8061 606/99 |
| 11,000,323 | B2 * | 5/2021 | Stamp | A61B 17/8061 |

* cited by examiner

*Primary Examiner* — Marcela I. Shirsat
(74) *Attorney, Agent, or Firm* — Wood, Phillips, Katz, Clark & Mortimer

(57) ABSTRACT

The combination of: a) a bone implant having a body with a first portion that overlies an outer bone surface and first and second projections; and b) a bone implant handling instrument comprising: a guide assembly; and an implant advancing assembly. With a part of the bone implant handling instrument bearing against at least one bone part, the bone implant can be guided by the instrument in substantially a straight line in a first direction, while being maintained in substantially a same orientation with respect to the straight line, between a starting position and an operative position. The implant advancing assembly has at least one part that is movable against the bone implant to advance it into the operative position wherein the first and second projections are advanced into one or more bone parts and the first portion of the body overlies an outer bone surface.

32 Claims, 14 Drawing Sheets

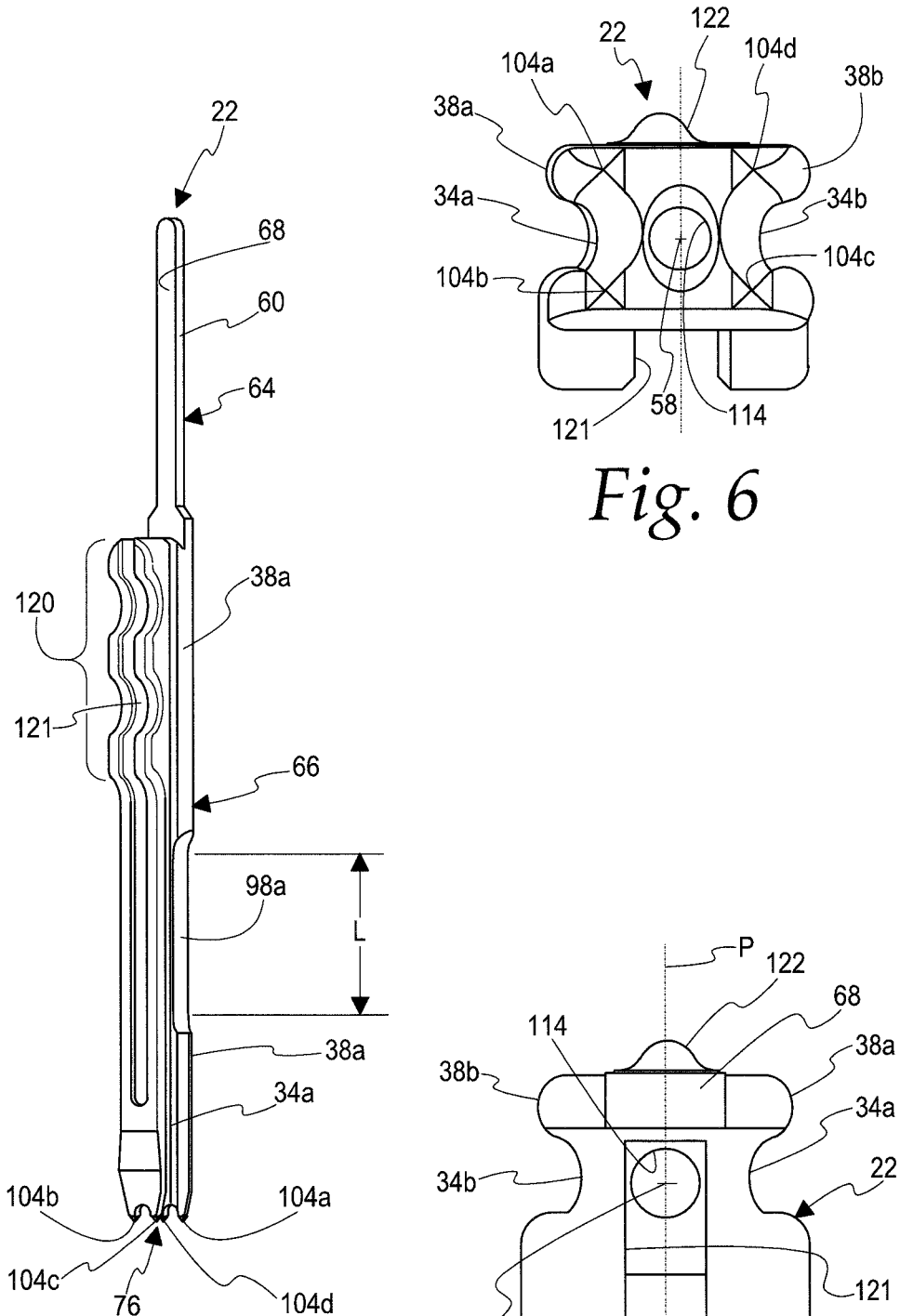

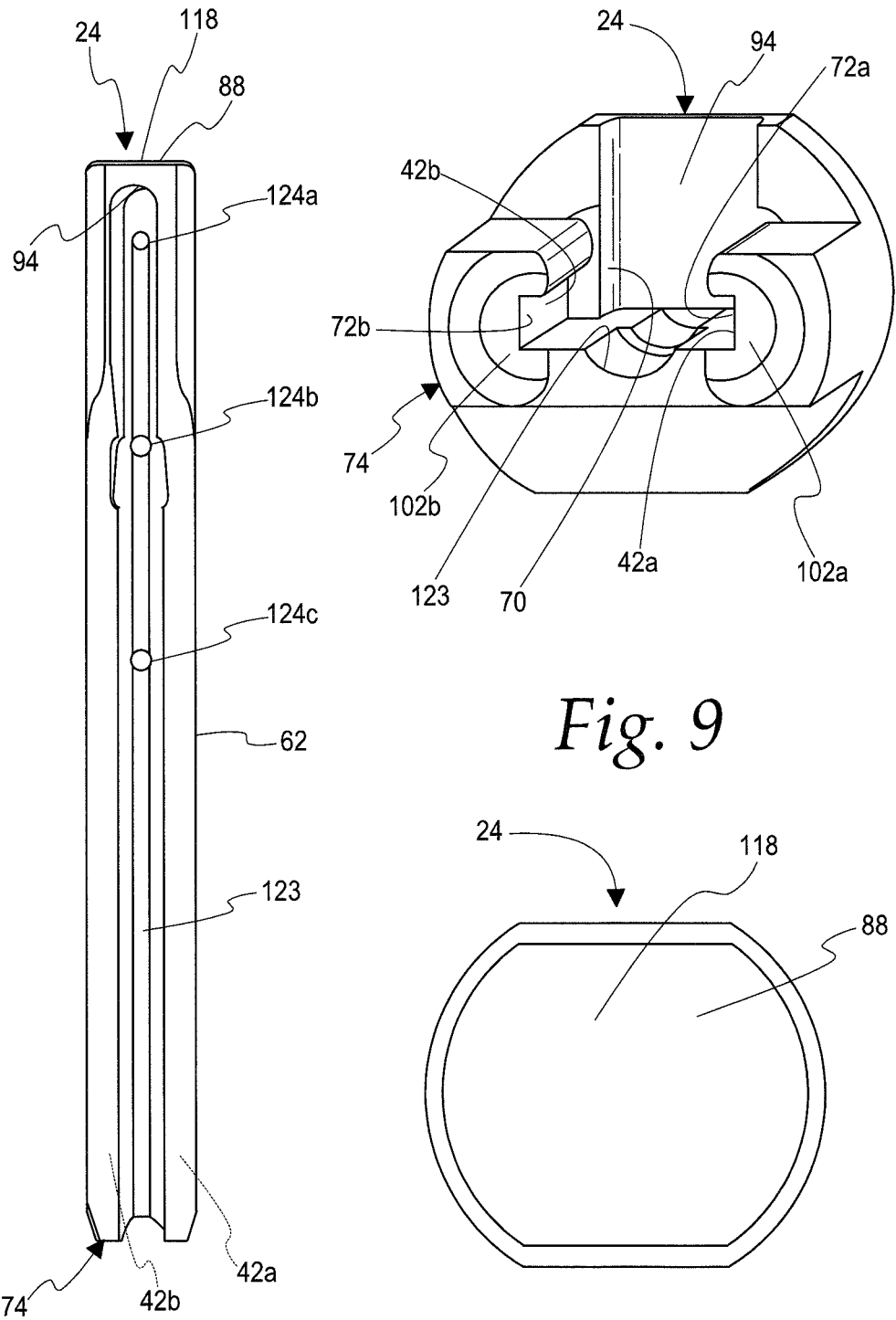

BONE IMPLANT HANDLING INSTRUMENT FOR PLACING A BONE IMPLANT IN AN OPERATIVE POSITION

CROSS-REFERENCE TO RELATED APPLICATIONS

This application is a continuation-in-part of U.S. patent application Ser. No. 16/875,760, filed May 15, 2020, which claims priority to Provisional Application No. 62/848,018, filed May 15, 2019, which are incorporated herein by reference.

BACKGROUND OF THE INVENTION

Field of the Invention

This invention relates to: a) bone implants and, more particularly, to a bone implant having one or more discrete projections that are advanced into one or more bone parts in placing the bone implant in an operative position; and b) a bone implant handling instrument for placing the bone implant in an operative position.

Background Art

Many different types of surgical procedures are performed using bone implants that have projections that are advanced into one or more bone parts in placing the bone implant in an operative position. This bone implant configuration, while having other applications, is commonly used to stabilize bone parts at a fracture site, in performing corrections/osteotomies, etc. Exemplary forms of such implants are commonly termed "hook plates", staples, formed wire, etc.

Hook plates are commonly used to achieve fixation of terminal bone fragments, relying upon the projections, making up at least part of each "hook", to be advanced into bone to effect internal purchase of a bone part to maintain the desired location of one fragment relative to other fragments and/or a stable bone part. Hook plates are commonly used for repair of wrist and ankle bones. Commonly, each hook plate has at least two projections which penetrate bone with the implant in its operative position.

It is known to pre-drill holes to accept the projections. The implant is commonly pre-connected to a device which can be controlled to drive the projections into the drilled holes. Once the securement of the implant to a device is effected, the device is used to reposition the implant and to facilitate driving of the projections into bone. The device is thereafter disconnected from the implant.

Certain prior art devices require the use of fasteners to secure the device to a plate region on the implant. Typically, a screw or other coupling component is advanced through a threaded aperture in the plate. Other forms use a clamp which extends to under the implant. Before the implant is finally fixed to the bone, the fasteners and/or clamp structure must be separated therefrom.

Typically, such devices are constructed so that once the device is separated from the implant, the implant must be driven an additional increment to become fully seated in its final operative position. This last step is necessitated by the fact that a portion of the implant must have sufficient projection away from the associated bone surface that it can be engaged by the device. Thus, with the device engaged, a flush insertion of the implant at the location of the projections using only the device is generally not achievable.

Still further, during the process of separating the device, preparatory to final positioning, the alignment and/or degree of bone purchase by the projections may be inadvertently altered or compromised.

This conventional practice is further complicated by the fact that in certain procedures, such as on wrists, the pre-drilled holes for the projections must be quite small and are potentially obscured from the surgeon's perspective by blood and adjacent tissue and further potentially by parts of the device residing in the line of sight between the surgeon and the drilled openings.

Several different forms of devices have been used to hold bone implants as projections thereon are advanced into bone to realize the operative position for the implant. Generally, these devices tend to be relatively complicated in construction and expensive to manufacture. Connection of implants to devices using fasteners and/or frictional engagement have also heretofore been potentially unreliable in terms of consistent alignment of the implant thereon and positive holding of the implant thereby.

Further, the above conventional devices, during setup and use, tend to require the performance of multiple steps by potentially more than one individual, which complicates procedures and may lead to lengthened operating times. An overriding objective in all surgical procedures is to avoid complication and minimize time so as not to unnecessarily challenge or fatigue surgeons. Simpler and more efficient procedures also reduce risk of infection.

Aside from the issues raised above, the generally elongate nature of such existing devices requires that the surgeon view the insertion step from a perspective substantially above the actual implant location. This may further impair the surgeon's ability to observe the initial placement of the implant projections and control insertion of the implant projections.

Still further, many existing devices are difficult to thoroughly clean and sterilize by reason of complicated geometry.

Another issue that arises is that it may be necessary to keep on hand different implant configurations and different driving devices that may be specifically designed for use with a specific implant configuration, and not others. This creates the need to have multiple driving devices available, which complicates inventory and potentially creates storage and access issues.

SUMMARY OF THE INVENTION

In one form, the invention is directed to the combination of: a) a first bone implant having a body with a first portion configured to overlie an outer bone surface with the first bone implant in an operative position and first and second projections; and b) a bone implant handling instrument comprising: a guide assembly; and an implant advancing assembly. Each of the first and second projections is configured to extend into at least one bone part with the first bone implant in the operative position. The first and second projections respectively have first and second free ends. The guide assembly and first bone implant are configured so that with a part of the bone implant handling instrument bearing against at least one bone part at a first location and the first bone implant operatively positioned with respect to the guide assembly, the first bone implant can be guided in substantially a straight line in a first direction, generally toward the first location, while being maintained in substantially a same orientation with respect to the straight line, between a starting position and the operative position. The implant advancing assembly has at least one part that is movable against the first bone implant to thereby drive the first bone implant from the starting position into the operative position wherein the first and second projections are advanced into one or more bone parts and the first portion of the body overlies an outer bone surface. The bone implant handling instrument and the first bone implant are configured so that, as an incident of the first bone implant being moved into the operative position, the bone implant handling instrument and first bone implant are in a relationship wherein the bone implant handling instrument can be moved away from the bone implant.

In one form, the at least one part is movable guidingly on the bone implant handling instrument.

In one form, the first bone implant and guide assembly define a cooperating rail and slot arrangement that guides the first bone implant in the straight line.

In one form, the guide assembly and implant advancing assembly define a cooperating rail and slot arrangement that causes the at least one part to be guided in a controlled path up to and against the operatively positioned first bone implant.

In one form, the bone implant handling instrument has a central longitudinal axis substantially aligned with the straight line.

In one form, the first bone implant and guide assembly define first and second cooperating rail and slot arrangements on opposite sides of a plane containing the longitudinal axis that guide the first bone implant in the straight line and that act to block reorientation of the first bone implant with respect to the straight line with the first bone implant moving in the straight line.

In one form, the first and second cooperating rail and slot arrangements have first and second slots on the guide assembly that open away from each other and first and second rails on the first bone implant that reside respectively in the first and second slots with the first bone implant operatively positioned with respect to the guide assembly.

In one form, the first bone implant and guide assembly are configured so that with the first bone implant operatively positioned with respect to the guide assembly, the first bone implant is releasably frictionally maintained in relationship to the guide assembly whereupon a force must be applied by a user to the first bone implant to move the first bone implant relative to the guide assembly in the straight line.

In one form, the implant handling instrument has a central longitudinal axis substantially aligned with the straight line. The rail and slot arrangement includes a rail on the guide assembly with spaced ends. The rail on the guide assembly has a discrete gap between the spaced ends that permits a part of the first bone implant to be advanced radially through the discrete gap to facilitate operative positioning of the first bone implant relative to the guide assembly.

In one form, the first and second projections make up a part of the rail and slot arrangement. The first and second projections are respectively guided in first and second slots on the guide assembly and cooperate to block reorientation of the first bone implant with respect to the straight line with the bone implant moving in the straight line.

In one form, the implement advancing assembly has an enlarged graspable head that moves as one piece with the at least one part of the implant advancing assembly. A user can manipulate the enlarged graspable head to drive the first bone implant from the starting position into the operative position.

In one form, the implement advancing assembly has a substantially flat impact surface that moves as one piece with the at least one part of the implant advancing assembly. A user can strike the impact surface to generate a force that is at an angle to a plane of the impact surface to thereby drive the first bone implant towards the operative position.

In one form, the part of the bone implant handling system that can be borne against at least one bone part at the first location has a plurality of feet each with a sharp tip to bear against at least one bone part at the first location.

In one form, the first and second projections have first and second substantially parallel lengths.

In one form, the first portion of the body is a formed plate.

In one form, the first portion of the body has a formed wire shape.

In one form, the first portion of the body has a formed wire shape and at least one plate fixed to the formed wire shape.

In one form, the guide assembly has an axially extending bore. The guide assembly is provided in further combination with a locating wire that is extendable into bone and slidable guidingly within the axially extending bore to facilitate placement of the bone implement handling instrument with respect to one or more bone parts preparatory to operatively positioning the first bone implant.

In one form, the first bone implant has facing surface regions between which a portion of the guide assembly resides. The facing surface regions and the portion of the guide assembly cooperate to block reorientation of the first bone implant with respect to the straight line with the first bone implant moving in the straight line.

In one form, the first bone implant has a convex "U" shape at first and second locations respectively where the first and second projections connect to the first portion of the body. The at least one part on the implant advancing assembly is movable against the convex "U" shapes at each of the first and second locations in driving the first bone implant into the operative position.

In one form, the at least one part has first and second discrete concave surfaces that bear one each against the convex "U" shapes.

In one form, the guide assembly has a contoured outside surface to accept a user's fingers to facilitate grasping of the guide assembly.

In one form, the first bone implant is in the form of a hook plate.

In one form, the first bone implant is in the form of a staple.

In one form, the first and second projections have facing substantially parallel surfaces that act against the guide assembly to guide movement of the first bone implant in the straight line and block reorientation of the first bone implant with respect to the straight line with the first bone implant moving in the straight line.

In one form, the guide assembly has substantially parallel surfaces that face away from each other, are substantially parallel to the facing surfaces, and cooperate one each with the facing surfaces to guide movement of the first bone implant in the straight line and block reorientation of the first bone implant with respect to the straight line with the first bone implant moving in the straight line.

In one form, the first cooperating rail and slot arrangement comprises a rail and slot on the guide assembly that respectively cooperate with a slot and rail on the first bone implant.

In one form, the first bone implant and guide assembly define a cooperating rail and slot arrangement that guides the first bone implant in the straight line. One rail defines a part of each of the cooperating rail and slot arrangements.

In one form, there is at least one detent component on each of the guide assembly and implant advancing assembly that cooperate to releasably consistently maintain the guide assembly and implant advancing assembly in first and second different predetermined relationships.

In one form, the above combination is provided in further combination with at least a second bone implant having a different configuration than the first bone implant. The at least second bone implant has a body with a first portion configured to overlie an outer bone surface with the at least second bone implant in an operative position, and first and second projections each configured to extend into at least one bone part with the at least second bone implant in its operative position. The at least second bone implant and bone implant handling instrument are configured so that the at least second bone implant can be used in place of the first bone implant to cooperate with the bone implant handling instrument in substantially a same manner as the first bone implant cooperates with the bone implant handling instrument so that with the second bone implant operatively positioned with respect to the guide assembly the bone implant handling instrument can be used to advance the second bone implant between a respective starting position and a respective operative position.

In one form, the first bone implant and at least second bone implant are configured to cooperate with different bones.

In one form, the first bone implant and at least second bone implant are configured to cooperate with a same bone.

BRIEF DESCRIPTION OF THE DRAWINGS

FIG. 5 is a perspective view of the guide assembly on the bone implant handling instrument in FIG. 4;

FIG. 6 is an angled bottom view of the guide assembly in FIG. 5;

FIG. 7 is a top view of the guide assembly in FIGS. 5 and 6;

FIG. 8 is an elevation view of the implant advancing assembly on the bone implement handling instrument in FIG. 4;

FIG. 9 is an enlarged, perspective view from a distal end of the implant advancing assembly in FIG. 8;

FIG. 10 is an enlarged, top view of the implant advancing assembly in FIGS. 8 and 9;

DETAILED DESCRIPTION OF THE PREFERRED EMBODIMENT

Figure 1:
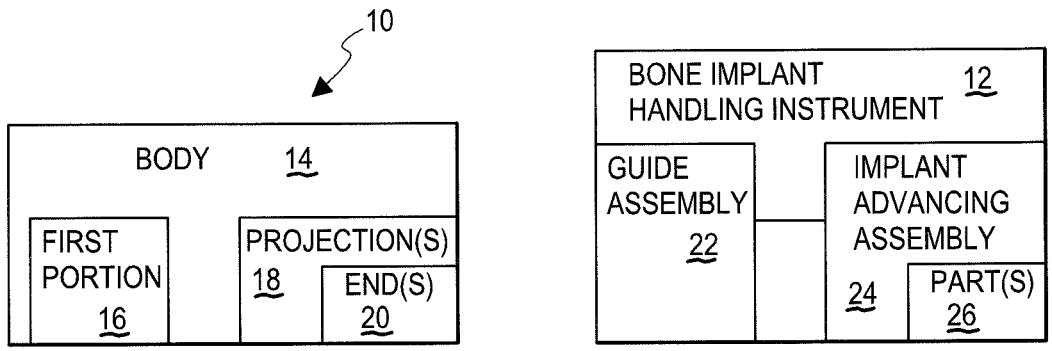
FIG. 1 is a schematic representation of a bone implant handling instrument, according to the present invention, together with a bone implant that can be used with the bone implant handling instrument to be placed into its operative position.

The present invention is directed to the combination of a bone implant, as shown schematically at 10 in FIG. 1, and a bone implant handling instrument 12, shown also schematically in FIG. 1, usable to place the bone implant 10 in an operative position during a surgical procedure.

The bone implant 10 has a body 14 with a first portion 16 and at least one projection 18. With the bone implant 10 in an operative position, the first portion 16 overlies an outer bone surface, and the at least one projection 18 extends into at least one bone part.

The schematic showing of the bone implant 10 is intended to encompass any bone implant that requires the penetration, and purchase, of bone by an integral part thereof, for the bone implant 10 to perform its function, whether it be to facilitate the stabilization of one or more bone fragments, stabilize a major bone fracture, stabilize bone parts during a correction/osteotomy, or otherwise contribute to the mounting of the bone implant 10 in its operative position to perform its intended function, which could be beyond simply stabilizing bone parts to facilitate repair of a fracture. The projections 18 each has a free end 20 that is directed into one or more bone parts during a procedure.

The schematic depiction of the bone implant 10 is intended to encompass implants utilized with any bone or bones, including stable portions and/or one or more fragments, and with any different configuration that may be adapted to one or more bones or to interact in different ways and/or at different bone locations. The schematic depiction is also intended to encompass any and all types of implant construction, to include but not limited to, those formed partially or entirely from wire, as in FIGS. 21 and 22, the constructions as in FIGS. 4-20, etc.

The bone implement handling instrument 12 consists of a guide assembly 22 and an implant advancing assembly 24. The guide assembly 22 and implant advancing assembly 24 may take a multitude of different forms, as represented by the schematic showing. The schematic showing is intended to encompass virtually an unlimited number of variations of each of the guide assembly 22 and implant advancing assembly 24, and their interaction, with the specific forms of the invention, described hereinbelow, being exemplary in nature only.

Some exemplary implant forms are disclosed in U.S. Pat. No. 8,821,508, to Medoff et al., the disclosure of which is incorporated herein by reference.

While the bone implant 10 is likewise capable of a multitude of different constructions and shapes, what is desirable is that the bone implement handling instrument 12 be constructed so that the guide assembly 22 and bone implant 10 are configured so that with a part of the bone implant handling instrument 12 bearing against at least one bone part at a first location and the bone implant 10 operatively positioned on the instrument 12 with respect to the guide assembly 22, the bone implant 10 can be guided in substantially a straight line in a first direction, generally towards the first location, while being maintained in substantially a same orientation with respect to the straight line, as it moves between a starting position and the operative position. In the latter position, the projection(s) 18 has penetrated at least one bone part and the first portion 16 overlies an outer bone surface.

The implant advancing assembly 24 has at least one part 26 that is movable against the bone implant 10 to thereby move/drive the bone implant 10 from the starting position into the operative position.

Further, the bone implant handling instrument 12 and bone implant 10 are configured so that as an incident of the bone implant 10 realizing the operative position, the bone implement handling instrument 12 can be separated from the bone implant 10. That is, the bone implant handling instrument 12 and bone implant 10 assume a relationship wherein they are effectively disconnected, thereby obviating the need to manipulate fasteners, clamps, or other separate parts.

While not required, the part(s) 26 is movable guidingly on the bone implement handling instrument 12.

Figure 2:
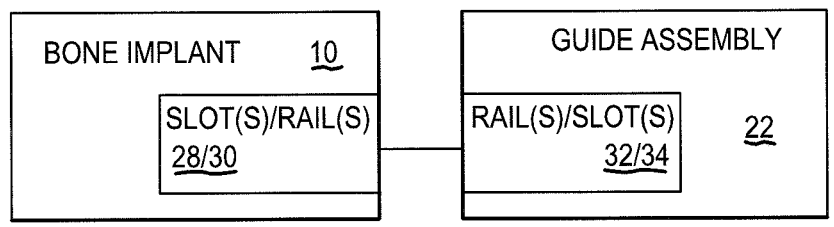
FIG. 2 is a schematic representation of a cooperating rail and slot arrangement provided on the bone implant and a guide assembly on the bone implant handling instrument.

As shown schematically in FIG. 2, the bone implant 10 is guided in the straight line through a cooperating rail and slot arrangement consisting of one or more slots/rails 28, 30 on the bone implant that cooperate(s) with one or more rails/slots 32, 34 on the guide assembly 22.

Figure 3:
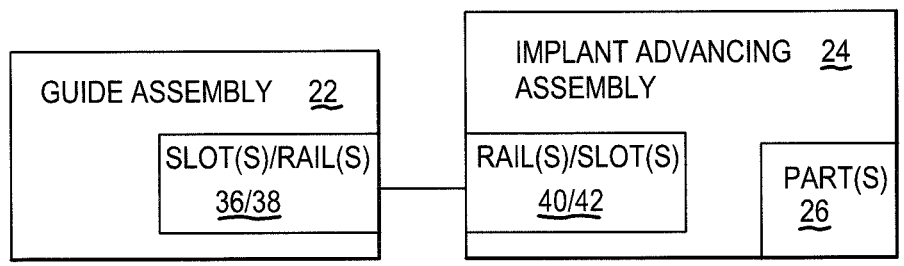
FIG. 3 is a schematic representation of a cooperating rail and slot arrangement provided on the guide assembly and an implant advancing assembly on the bone implant handling instrument.

As shown in FIG. 3, the at least one part 26 on the implant advancing assembly 24 is movable relative to the guide assembly 22 through a cooperating rail and slot arrangement consisting of at least one slot/rail 36, 38 on the guide assembly 22 that cooperate(s) with at least one rail/slot 40, 42 on the implant advancing assembly 24. Through this arrangement, the at least one part 26 is guided in a controlled path up to and against the operatively positioned bone implant.

The schematic showing of the cooperating rail and slot arrangements in FIGS. 2 and 3 is intended to encompass a multitude of different combinations of cooperating rails and slots. For example, a single rail and slot may be provided, one each on the bone implant 10 and guide assembly 22 and/or on the guide assembly 22 and implant advancing assembly 24. Multiple rail and slot pairs may be provided in spaced relationship or in adjacent relationship wherein there are alternating arrangements of rails and slots in close enough proximity to provide greater stability and positively control the relationship between the components on which the rails and slots are provided.

It is preferred that the rail and slot arrangements be such that they cooperate so as to be primarily responsible for maintaining the orientation of the bone implant 10 with respect to the straight line path as it moves between the starting and operative positions.

Each generic rail and slot configuration contemplated typically involves at least two surfaces on the rail that cooperate with two surfaces on the slot. The two surfaces on each rail and slot may be spaced and commonly are transverse to confine multidimensional movement between the components in which each rail and slot are each provided. The rail and slot arrangements may each perform in certain configurations as a conventional sliding tongue-and-groove arrangement.

In one preferred form, the cooperating rail arrangement on the bone implant 10 and guide assembly 22 may be such that at approximately the same location there is both a rail and a slot on each of the bone implant 10 and guide assembly 22 that cooperate in a complementary fashion.

Further, the rail and slot arrangement cooperating between the bone implant 10 and guide assembly 22 may be completely independent of the rail and slot arrangement cooperating between the guide assembly 22 and implant advancing assembly 24. Alternatively, there may be a sharing of some or all of the slots and rails.

One specific exemplary form of each of the bone implant 10 and bone implant handling instrument 12 will be described with respect to FIGS. 4-20, below.

The bone implant 10 consists of the aforementioned body 14 having the first portion 16 and first and second projections 18a, 18b having, as depicted, mirrored corresponding shapes.

The first body portion 16 is in the form of a substantially rectangular plate 44 with a bottom surface 46 to be placed at least nominally conformingly in overlying and adjacent or abutting relationship with an outer bone surface with the bone implant in its operative position. A series of apertures 48 are formed through the plate 44 and may have strategically selected circular and elongate shapes, with and/or without threads, to accept suitable fasteners usable to maintain the plate 44 fixed relative to the underlying bone.

The apertures 48 are in either colinear or staggered off-center orientation relative to a longitudinal axis of the body, and may include countersunk, beveled perimeters facilitating the frusto-conical heads of conventional bone screws to be fully seated against, and hence in securing engagement with, an associated aperture upon implantation.

The projections 18a, 18b each makes an acute angle θ with the bottom surface 46 of the plate 44.

Curved connecting regions 50a, 50b extend between the plate 44 and the projections 18a, 18b, respectively. The plate 44, connecting region 50a, and projection 18a cooperatively define an inverted "U" shape with a convexly curved surface 52a at the base of the "U". The plate 44, curved connecting region 50b, and projection 18b have a like construction to produce a like, convexly curved surface 52b at the base of the respective "U" shape.

The projections 18a, 18b have aligned lengths that reside substantially in a common plane. Facing surfaces 54a, 54b on the projections 18a, 18b are substantially flat and in parallel, spaced relationship.

The projections 18a,18b have respective, sharp free ends 56a, 56b and a cross-section transversely to their length that progressively diminishes towards the free ends 56a, 56b, thereby producing shapes that penetrate bone through a progressive wedging action as the projections 18a, 18b are advanced lengthwise with the free ends 56a, 56b in a leading position.

The curved regions 50a, 50b and projections 18a, 18b are strategically matched to cooperating parts on the bone implant handling assembly 12 to facilitate the aforementioned interaction, as described in greater detail below.

It should be emphasized that this bone implant configuration is but exemplary in nature and is what is commonly identified as a hook plate used conventionally to set a desired relationship between stable and unstable bone parts and bone fragments. The particular application is not limited nor are the structural details thereof critical to understanding the present invention.

The bone implant handling assembly 12 has an elongate shape with a central longitudinal axis 58.

The guide assembly 22, the details of which are seen most clearly in FIGS. 5-7, has an elongate body 60 with a length aligned with the axis 58.

The guide assembly 22 and implant advancing assembly 24, the details of which are seen most clearly in FIGS. 8-10, are configured so that the body 60 on the guide assembly 22 moves guidingly within and relative to an elongate body 62 on the implant advancing assembly 24.

As depicted, the body 62 of the implant advancing assembly 24 has a generally obround shape as viewed along its lengthwise axis. The body 62 is cut away to receive a portion of the body 60 on the guide assembly 22.

The guide assembly body 60 has a proximal region 64 and a more distal region 66 that cooperate with the body 62 on the implant advancing assembly 24 in different manners to guide lengthwise relative movement between the guide assembly 22 and implant advancing assembly 24.

The proximal region 64 consists of an elongate tongue/rail 68 with a generally rectangular cross-sectional configuration that moves in a complementarily-shaped channel/slot 70 in the implant advancing assembly body 62.

The region 66 includes rails 38a, 38b on opposite sides of a plane P containing the instrument axis 58. In this embodiment, the body 60 is symmetrical on opposite sides of the plane P. The rails 38a, 38b are elongate with lengths substantially parallel to the axis 58.

The rails 38a, 38b respectively cooperate with complementarily-shaped slots 42a, 42b on the implant advancing assembly 24. The slots 42a, 42b respectively have surfaces 72a, 72b that face/open towards each other in a captively engaging relationship with the rails 38a, 38b.

With this arrangement, the guide assembly 22 and implant advancing assembly 24 are relatively movable lengthwise between: a) a first relationship wherein the distal end 74 of the implant advancing assembly 24 resides as shown in dotted lines in FIG. 4; and b) a second relationship wherein the end 74 projects to the distal end 76 of the guide assembly 22, as described in greater detail below.

The implant 10 has slots 28a, 28b, respectively with curved surfaces 80a, 80b which face/open towards each other. The slots 28a, 28b reside on opposite sides of the aforementioned reference plane P.

The slots 28a, 28b respectively cooperate with rails 38a, 38b on the guide assembly 22. As noted above with respect to FIGS. 2 and 3, the cooperating slot and rail arrangements may share rails between different components. In this case, the guide assembly rails 38a, 38b that guide the implant advancing assembly 24 are also utilized to guide the bone implant 10.

The projections 18a, 18b, in addition to being secured with respect to bone, also function, and will be considered the same as, the schematically depicted rails 30 and cooperate respectively with slots 34a, 34b on the guide assembly 22. The slots 34a, 34b have oppositely facing/opening surfaces 82a, 82b against which the surfaces 54a, 54b on the projections 18a, 18b respectively confront. The surfaces 54a, 54b, 82a, 82b are substantially parallel and guide lengthwise movement between the implant 10 and the guide assembly 22. The widths W1 of the slots 34a, 34b are slightly greater than the complementary widths of the projections 18a, 18b, thereby to create a sliding tongue-in-groove type of arrangement.

The guided movement of the projections 18a, 18b in the slots 34a, 34b causes the portions of the projections 18a, 18b that have not penetrated bone to be stabilized against bending as the projections are progressively pressed into bone. This same cooperation may assist in maintaining a consistent relationship/alignment between the projections 18a, 18b as they are advanced into bone. This is the case whether the projections are straight over only a portion of their lengths or have no precisely straight extent.

With this arrangement, there are multiple adjacent cooperating slot and rail arrangements on each side of the aforementioned reference plane P. The slot and rail arrangements guide the implant 10 in a substantially straight line path and at the same time maintain the implant in substantially the same orientation with respect to the straight line while likewise blocking radial shifting of the implant 10 in any direction away from this line during movement in operation. Alignment of the implant 10 is more positively maintained by moving the cooperating rail and slot bounding surfaces at different angles to control multidimensional relative movement between associated components.

The bone implement handling instrument 12 further includes an enlarged graspable head 84 that is provided with a receptacle 86 that matches the cross-section of the proximal end 88 of the implant advancing assembly 24. By directing the proximal end 88 into the receptacle 86, a keyed connection is established and maintained by a fastener 90 directed radially through an opening 92 in the head 84 and into a receptacle 94 on the implant moving assembly 24. With this arrangement, the head moves as one piece with the body 62.

The head 84 has a bulged, larger diameter region with circumferentially spaced contours 96a that, together with the overall shape, facilitate grasping in the hand of a user. A bulged, smaller diameter region has like contours 96b. By grasping the head 84, the user can readily turn the entire instrument 12 about the axis 58 and controllably and forcibly translate the implant advancing assembly 24 guidingly relative to the guide assembly 22. The two graspable diameters facilitate one- or two-handed grasping and operation.

To facilitate connection between the implant 10 and guide assembly 22, the rails 38a, 38b are provided with like discrete gaps 98a, 98b between their ends. The exemplary gap 98a on the guide rail 38a is shown in FIG. 5. The rail 38b has a like gap that is not shown in FIG. 5. The gaps 98 have a length L slightly greater than the length dimension L1 of the projections 18a, 18b.

Figure 4:
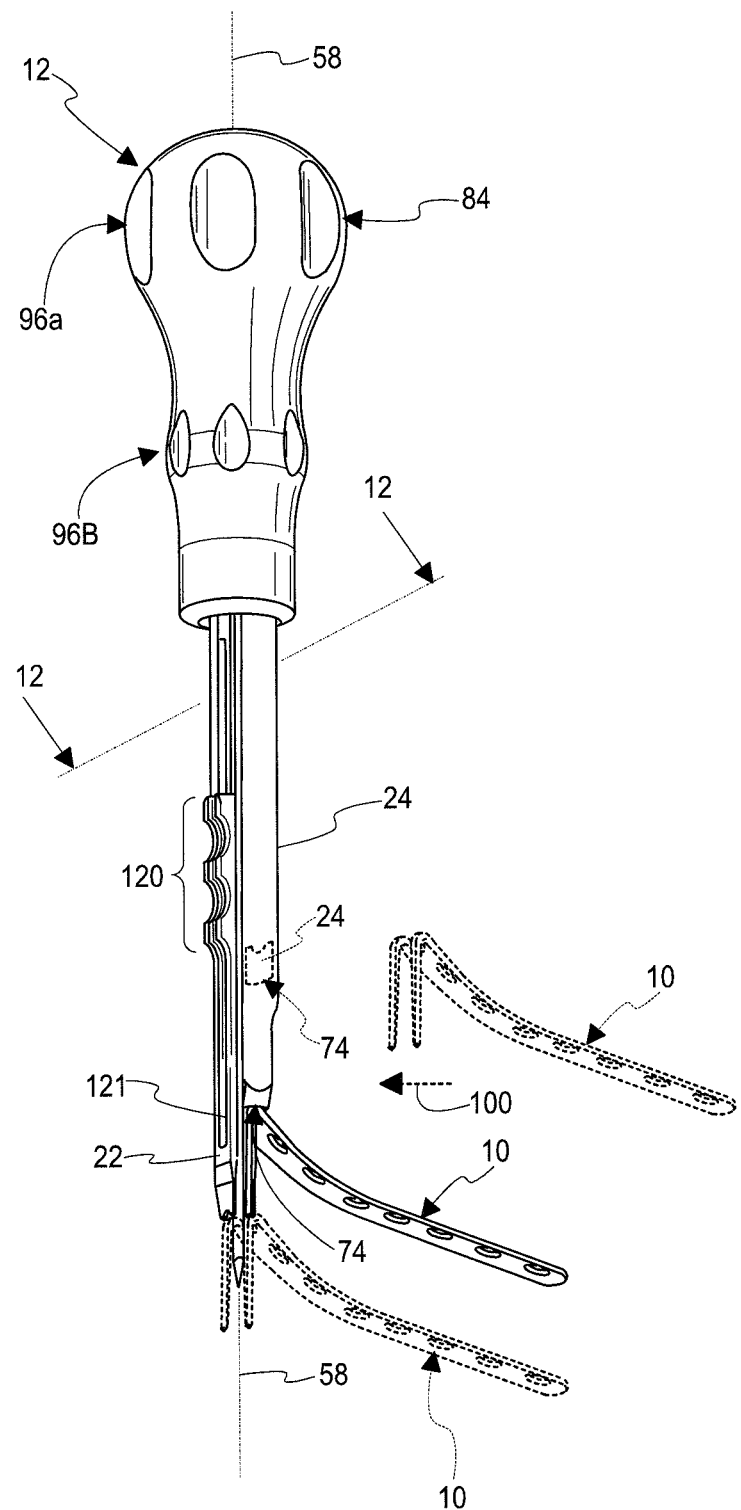
FIG. 4 is an elevation view of one form of bone implant handling instrument, as shown schematically in FIGS. 1-3, with a bone implant operatively positioned thereon.
Figure 11:
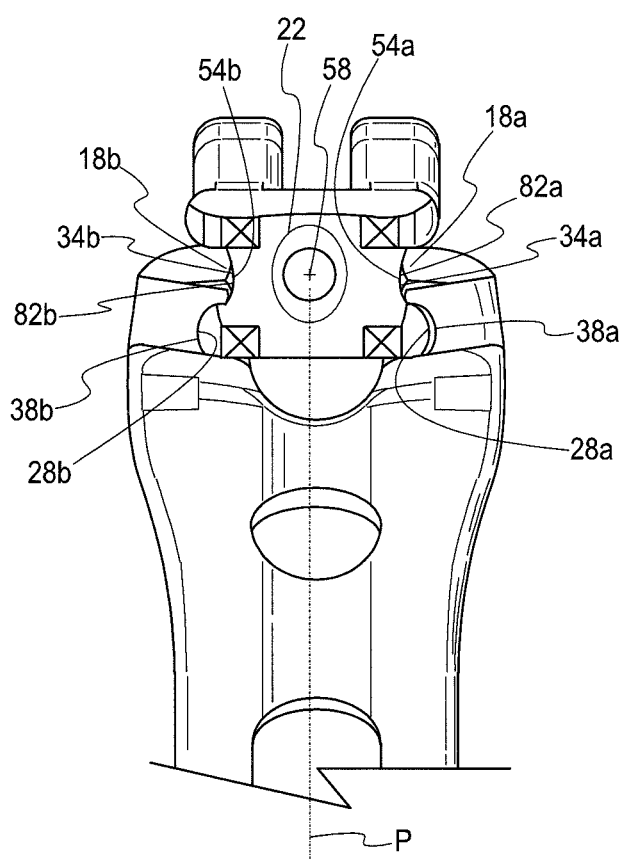
FIG. 11 is an enlarged, fragmentary, end view of the guide assembly in FIGS. 5-7 with the bone implant operatively positioned thereon.
Figure 12:
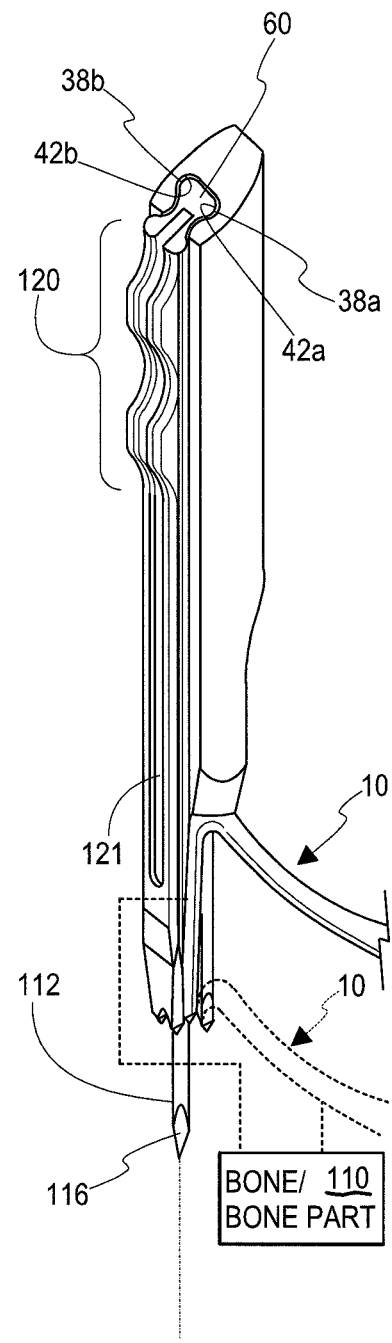
FIG. 12 is an enlarged, fragmentary, perspective view of the bone implant handling instrument shown cross-sectioned along line 12-12 of FIG. 4.
Figure 13:
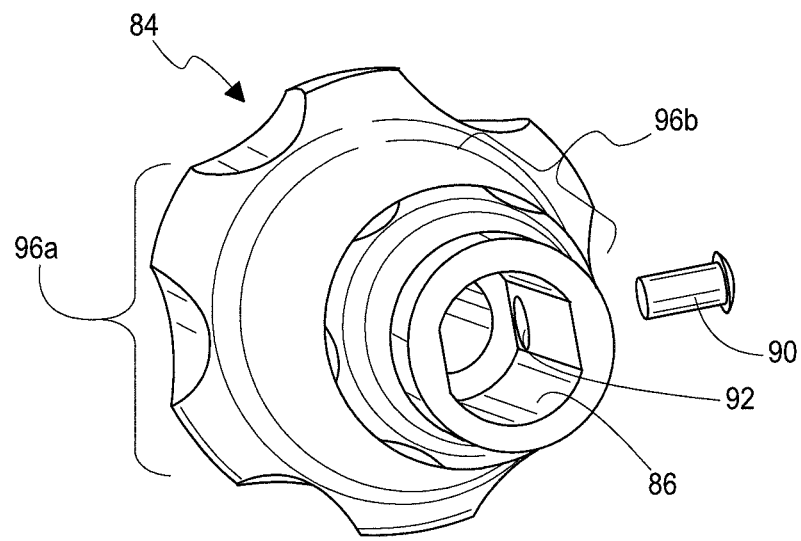
FIG. 13 is an enlarged, perspective view of a graspable head at the proximal end of the bone implant handling instrument in FIG. 4.
Figure 14:
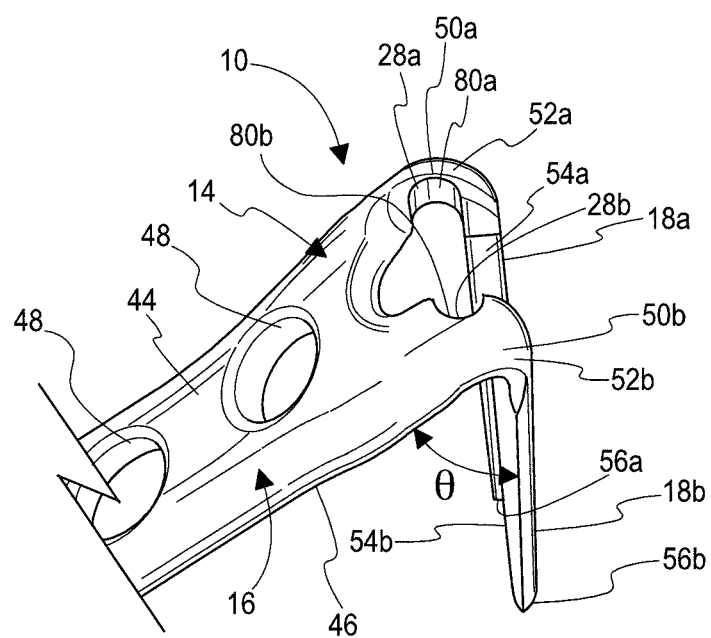
FIG. 14 is an enlarged, fragmentary, perspective view of the bone implant as shown in FIGS. 4, 11, and 12.
Figures 15, 16:
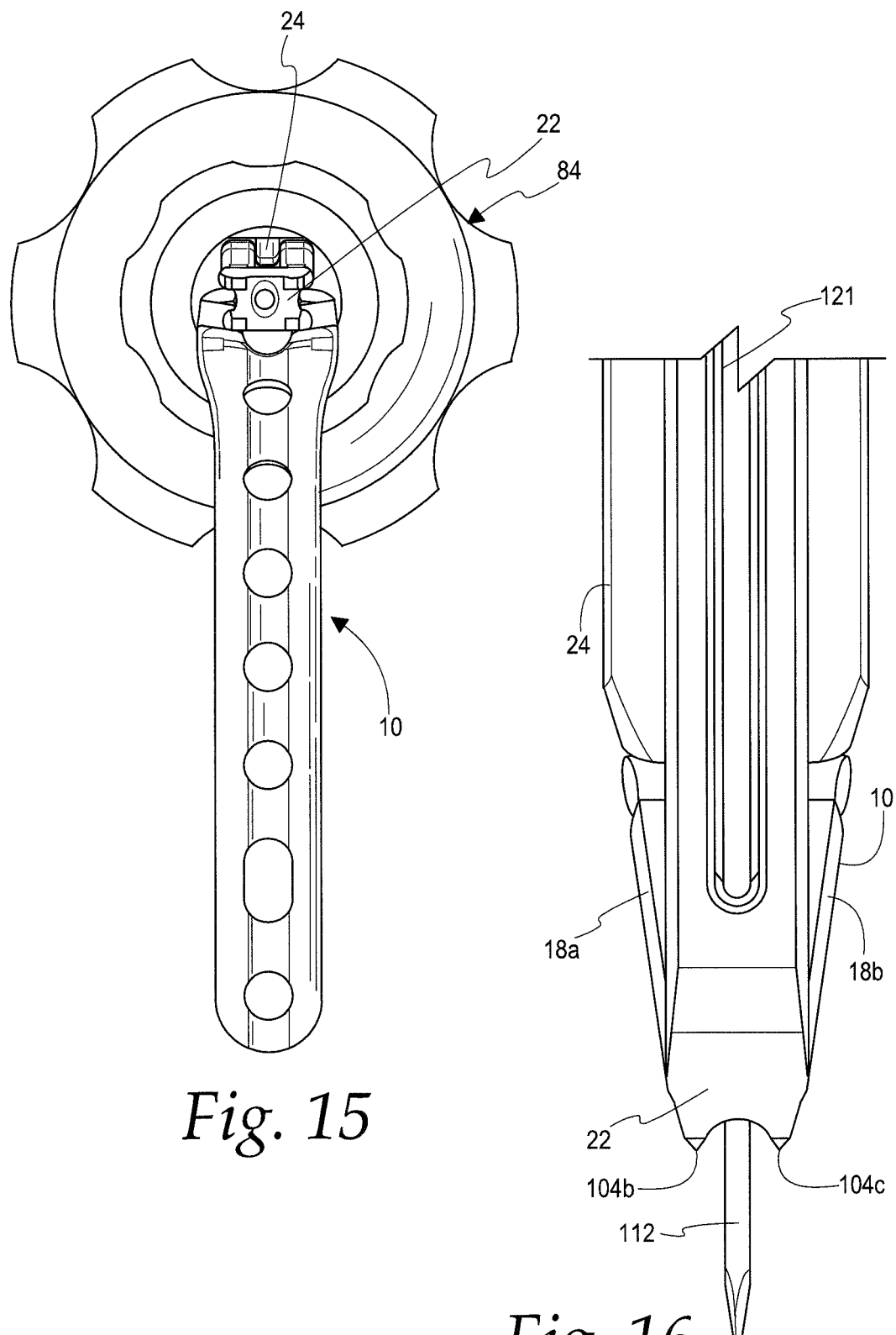
FIG. 15 is an end view of the bone implant handling instrument with the bone implant operatively positioned as in FIG. 4.
FIG. 16 is an enlarged, fragmentary view of a distal region of the bone implant handling instrument with the bone implant operatively positioned as shown in FIG. 4.
Figure 17:
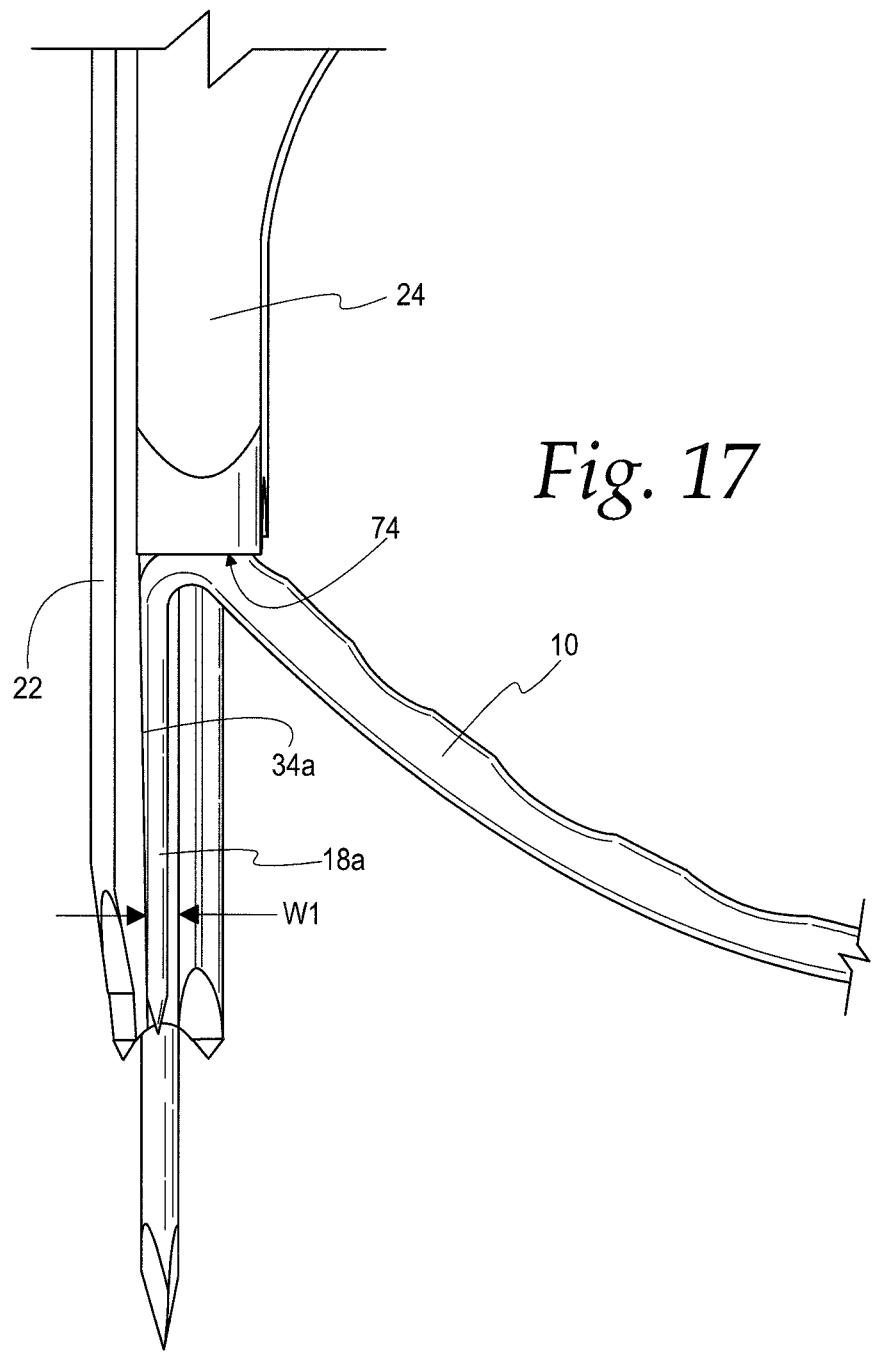
FIG. 17 is a view as in FIG. 16 from a different perspective.

To operatively position the bone implant 10, the implant advancing assembly 24 is moved to the dotted line position in FIG. 4 wherein the distal end 74 resides above the gaps 98 so that the gaps 98 are fully exposed. This allows the implant 10 to be advanced radially from a spaced location, in the top dotted line position, in the direction of the arrow 100 to place the projections 18a, 18b in alignment with the slots 34a, 34b on the guide assembly 22. At the same time, the rails 38a, 38b align lengthwise with the slots 28a, 28b.

The implant 10 and guide assembly 22 are relatively dimensioned so that the cooperating rail and slot bounding surfaces interact to create frictional forces that releasably maintain the implant against free sliding in the aforementioned first line parallel to the axis 58. Thus, a predetermined force must be applied to guidingly move the implant 10 downwardly along the guide assembly 22.

With the projections 18a, 18b introduced to their cooperating slots 34a, 34b, the implant is in the aforementioned starting position.

Figures 18, 19:
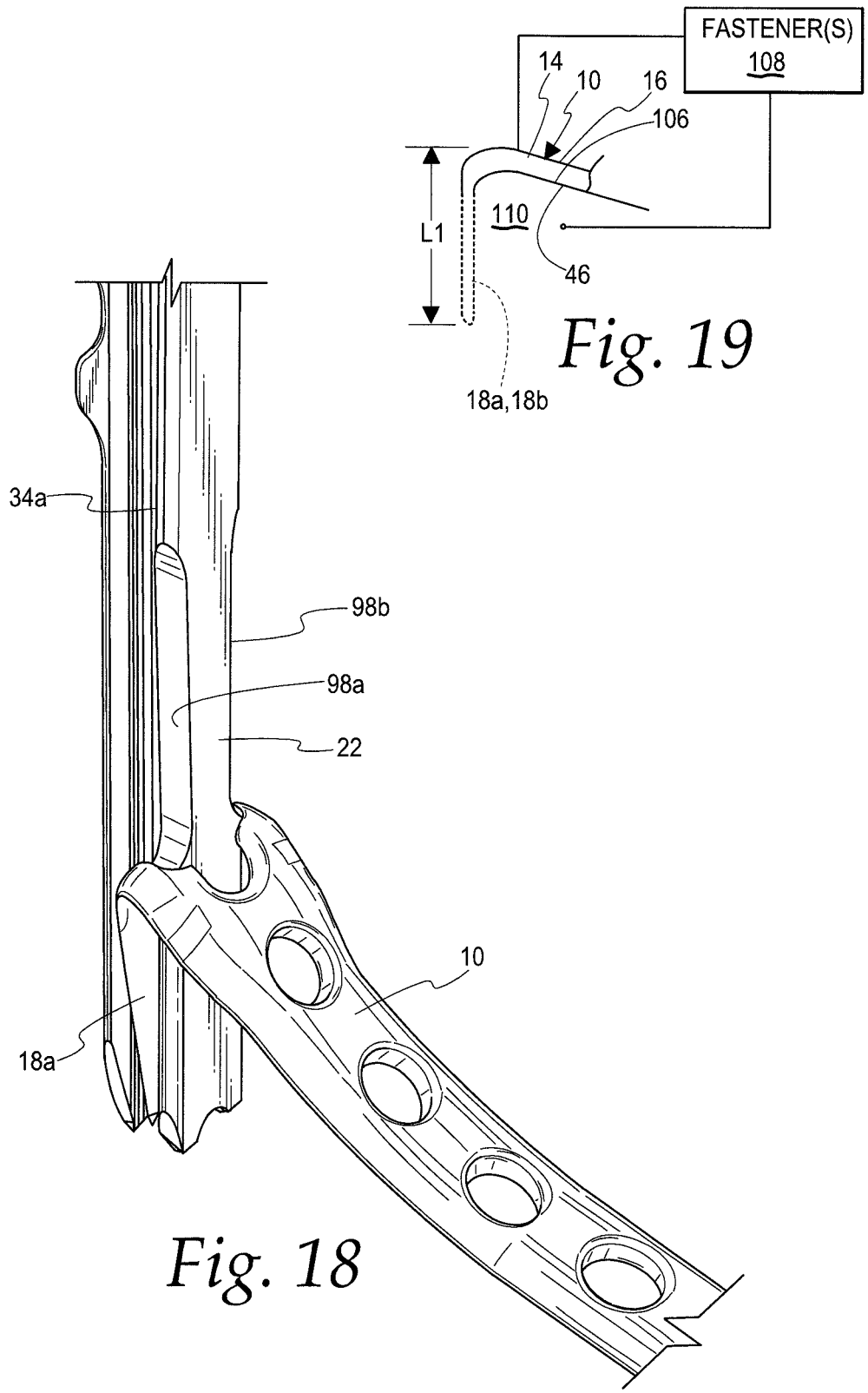
FIG. 18 is an enlarged, fragmentary, perspective view of a distal region of the guide assembly on the bone implant handling instrument in FIG. 4 with the bone implant operatively positioned thereon.
FIG. 19 is a fragmentary view of the bone implant as shown in FIGS. 4 and 14, operatively positioned with respect to a bone.
Figure 20:
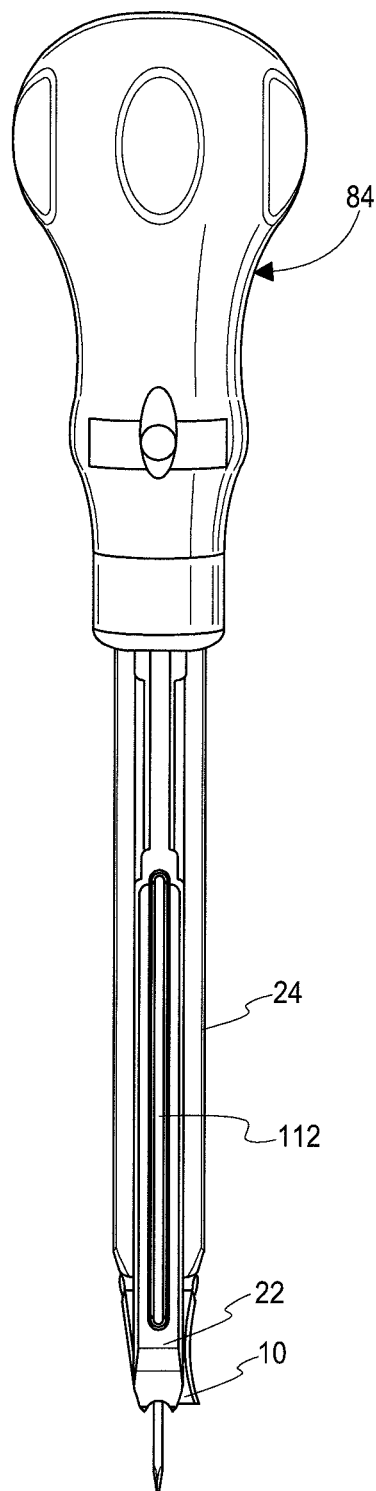
FIG. 20 is a view as in FIG. 4 from a different perspective.

From the starting position, the implant 10 is guidingly movable downwardly into its operative position wherein it is fully implanted through the instrument as shown in FIG. 19. The implant 10 is capable of translating from the starting position along the axis 58 to beyond the end 76 of the guide assembly 22 whereby the implant fully separates from the guide assembly 22.

Movement of the implant 10 from its starting position into its operative position is effected through the implant advancing assembly 24.

The distal end 74 is provided with concave, axially downwardly opening surfaces 102a, 102b that can be placed in complementary fashion, one each, over the convexly curved surface portions 52a, 52b on the operatively positioned implant 10. Moving the implant advancing assembly 24 downwardly from the dotted line position in FIG. 4 causes the surface portions 52a, 52b to nest in the complementary shapes bounded by the surfaces 102a, 102b, whereupon continued movement of the implant advancing assembly 24 translates the implant in its straight line path relative to the guide assembly 22. With this arrangement, the surfaces 102a, 102b act against the convex implant shapes at spaced locations, which produces a balanced force that reduces the tendency of the implant to skew as it is translated.

To facilitate precise placement of the implant at a selected location using the instrument 12, the guide assembly 22 has a plurality of projecting feet 104a, 104b, 104c, 104d, each having flat sides bounding a shape that tapers to a sharp tip. The feet 104 are arranged in a substantially square pattern equidistantly from the axis 58.

By pressing the feet 104 against one or more bone parts, the feet 104 at least superficially dig into the bone to prevent shifting relative thereto.

In a typical procedure, the feet 104 are borne against a bone at a location at which the projections 18a, 18b are to be inserted. The bone implant 10 can be operatively positioned either before this takes place or afterwards. The implant advancing assembly 24 is retracted to allow the implant 10 to be placed through the gaps 98 and can be shifted downwardly to engage the projections 18a, 18b with the cooperating slots 34a, 34b—this representing the aforementioned starting position.

The implant advancing assembly 24 can then be translated to move the implant 10 in its straight line path in a first/downward direction while being maintained in the same orientation with respect to the straight line. The implant 10 continues to be advanced until it realizes the operative position of FIG. 19 and as shown in dotted lines in FIG. 12, and in the lower dotted line position in FIG. 4. Once the implant projections 18a, 18b are fully seated, the instrument 12 can be readily separated since the instrument 12 and implant 10 are effectively disconnected as an incident of the bone implant being placed in its operative position. In the operative position, the bottom surface 46 of the implant 10 is at or against a bone surface 106 whereupon one or more fasteners 108 can be utilized to fix the first portion 16 of the body 14 to the underlying bone/bone part 110.

It is also contemplated that the implant 10 might be advanced relative to the guide assembly 22 so that the free ends 56a, 56b extend beyond the feet 104 whereby the free ends 56a, 56b contact bone, or enter pre-drilled bores, at the projection insertion location, before the feet engage bone to stabilize the instrument 12 at the initiation of the procedure.

Optionally, a locating wire 112 can be used to precisely position the instrument 12 preparatory to a procedure. The guide assembly 22 has an axially extending bore 114 with a complementary shape that allows sliding of the guide assembly 22 guidingly along the wire 112.

Conventional-type wires with a sharpened/pointed free end 116 are available that can be driven into the bone at the first location at which the projections 18 are to be implanted. The locating component may be a K-wire, pin, drill, etc.

The locating element can also be used to cooperate with other cannulated instruments, such as a double-barreled drill guide usable to assist formation of pilot holes for the leading ends of the projections 18a, 18b. Such a drill guide is disclosed in U.S. Patent Publication No. 2015/0134011, to Medoff, the disclosure of which is incorporated herein by reference. It is also possible to extend the locating wire 112 axially into or through the head 84.

With the same, above instrument configuration, the implant 10 might be selectively advanced in either of two different manners. As described above, the entire instrument 12 may be repositioned by grasping the head 84. The same head 84 is used to reposition the implant advancing assembly 24. As noted, the contoured outside surface of the head 84 accepts a user's fingers to allow a positive grasping of the head 84.

By removing the fastener 90 and separating the head 84 from the body 62 of the implant advancing assembly 24, a generally flat surface 118 is exposed at the end 88 which can be struck/impacted by a weighted object. Striking the impact surface 118 generates a force at an angle to the plane of the surface to thereby advance the operatively positioned implant into its operative position.

To facilitate handling and repositioning of the instrument 12, the body 60 of the guide assembly 22 is provided with a contoured region at 120 that defines complementary receptacles for individual user fingers, thereby allowing the circumference of the instrument 12 to be grasped at this region.

The body 60 has an elongate opening 121, that bisects the contoured region, thereby creating additional edges which can be gripped as well as reducing material and opening up different regions for easier and more effective cleaning.

In the depicted embodiment, the tongue 68 on the implant advancing assembly 24 has a detent component 122 in the form of a curved projection which aligns with, and is movable along a complementary lengthwise groove 123, into any of three detent receivers 124a, 124b, 124c with the guide assembly 22 and implant advancing assembly 24 in three different lengthwise relative positions. The detent arrangement allows the user to sense different significant relationships, including fully extended and fully retracted positions desired for the bone implant handling assembly 12, and also the position of the bone implant handling assembly 12 at which the gaps 98 are exposed to allow the implant to be operatively positioned.

Figure 21:
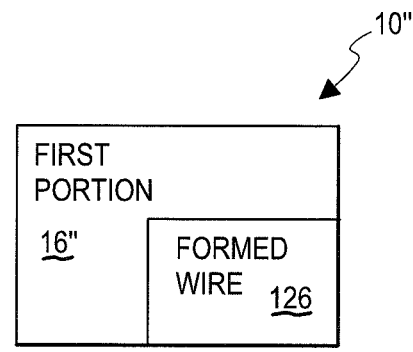
FIG. 21 is a schematic representation of a modified form of bone implant, according to the invention.

As noted above, the implant 10 is not limited to the exemplary form described hereinabove. As shown in FIG. 21, another generic form of implant 10" may have a first portion 16" with a formed wire 126.

Figure 22:
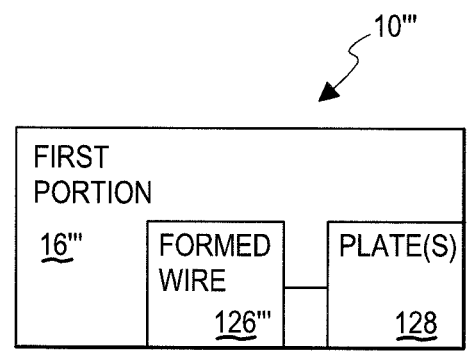
FIG. 22 is a schematic representation of a further modified form of bone implant, according to the invention.

In FIG. 22 an implant 10'" has a first portion 16'" with a formed wire 126'" and at least one plate 128 fixed to the formed wire 126'"—permanently or releasably.

Figure 23:
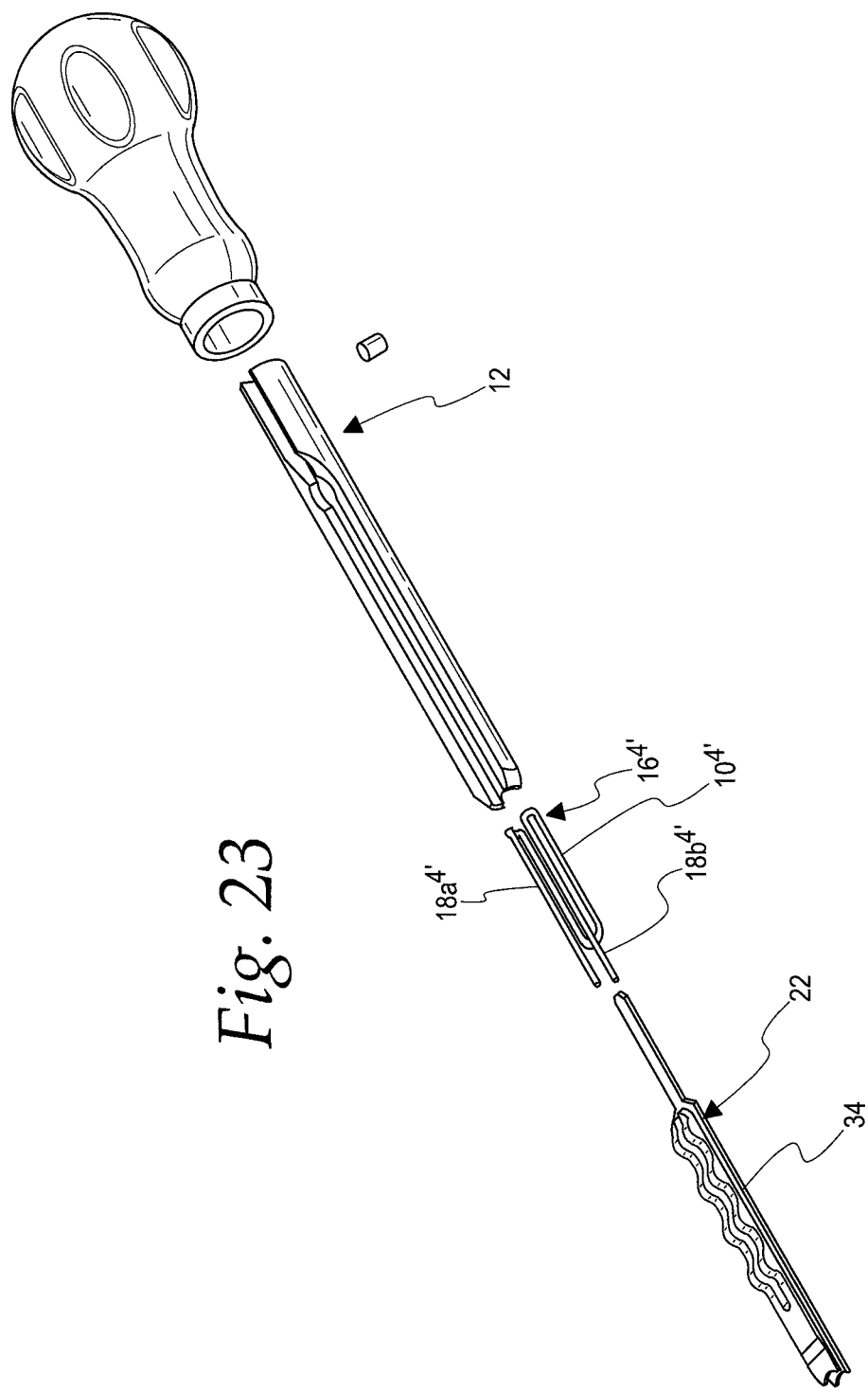
FIG. 23 is an exploded perspective view of a bone implant handling instrument, as shown in FIG. 4, with another form of bone implant aligned to be operatively positioned thereon.
Figure 24:
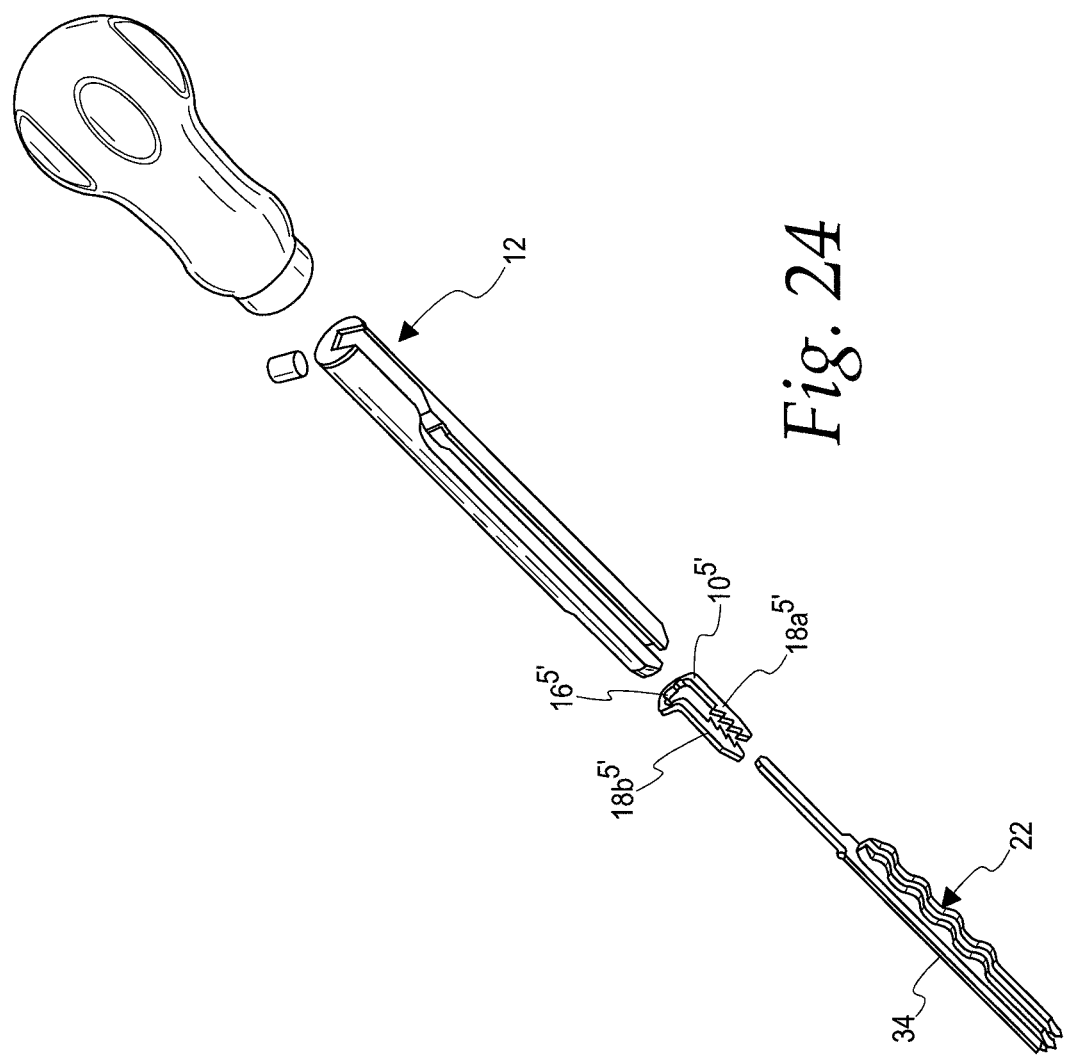
FIG. 24 is a view as in FIG. 23 with a further modified form of implant.
Figure 25:
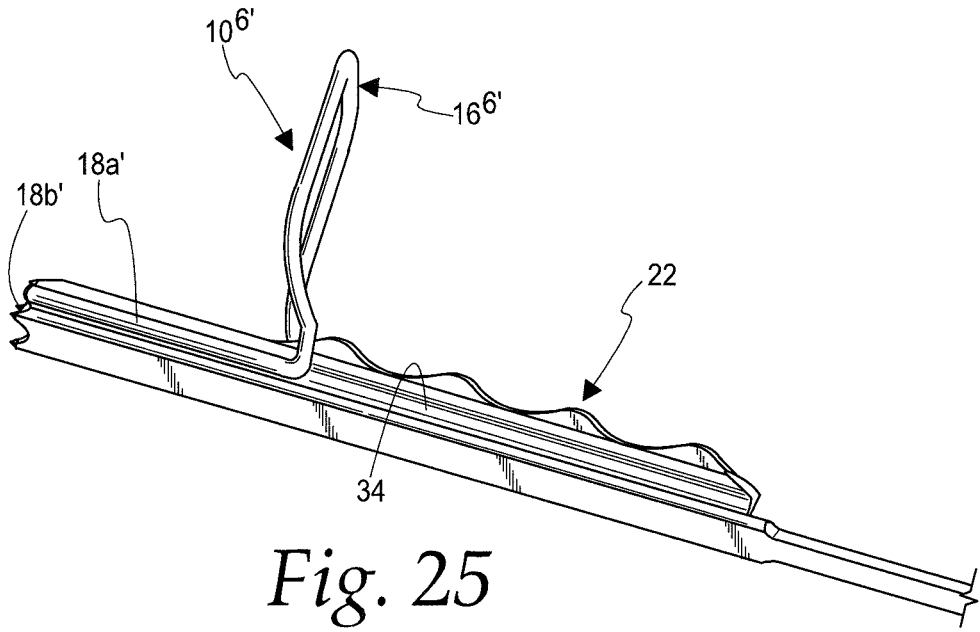
FIG. 25 is a perspective view of a guide assembly, as shown in FIGS. 23 and 24, with another form of implant situated to be operatively positioned thereon.

Specific alternative implant configurations are shown in FIGS. 23-25 in association with the bone implant handling instrument 12.

In FIG. 23 an implant $10^{4'}$ has a formed wire construction and is a type sold by the Applicant herein under the trademark "SLED". The implant $10^{4'}$ has a wire formed first portion $16^{4'}$ and spaced wire projections $18a^{4'}$, $18b^{4'}$. The first portion $16^{4'}$ and projections $18a^{4'}$, $18b^{4'}$ have generally aligned lengths.

The projections $18a^{4'}$, $18b^{4'}$ straddle and frictionally engage the guide assembly 22 and move guidingly within the rails 34 (one shown).

The implant $10^{5'}$ in FIG. 24 is in the form of a staple with projections $18a^{5'}$, $18b^{5'}$ which have saw-toothed edges and parallel lengths. The projections $18a^{5'}$, $18b^{5'}$ straddle the guide assembly 22 and move guidingly within the rails 34 (one shown) on the guide assembly 22. The first portion $16^{5'}$ connects between the projections $18a^{5'}$, $18b^{5'}$ and projects substantially orthogonally away from the plane thereof to overlie an outside bone surface upon being operatively positioned.

In FIG. 25, another form of implant $10^{6'}$ is shown, as currently offered by Applicant as its "Volar Buttress" implant. The implant $10^{6'}$ has elongate, substantially parallel, projections $18a^{6'}$, $18b^{6'}$ which frictionally straddle the guide assembly 22 and move guidingly within the rails 34 (one shown). The first portion $16^{6'}$ is a formed wire shape with a different angular relationship to the plane of the projections $18a^{6'}$, $18b^{6'}$ than the first region $16^{4'}$ is with the plane of the projections $18a^{4'}$, $18b^{4'}$ on the implant $10^{4'}$ in FIG. 23.

Figure 26:
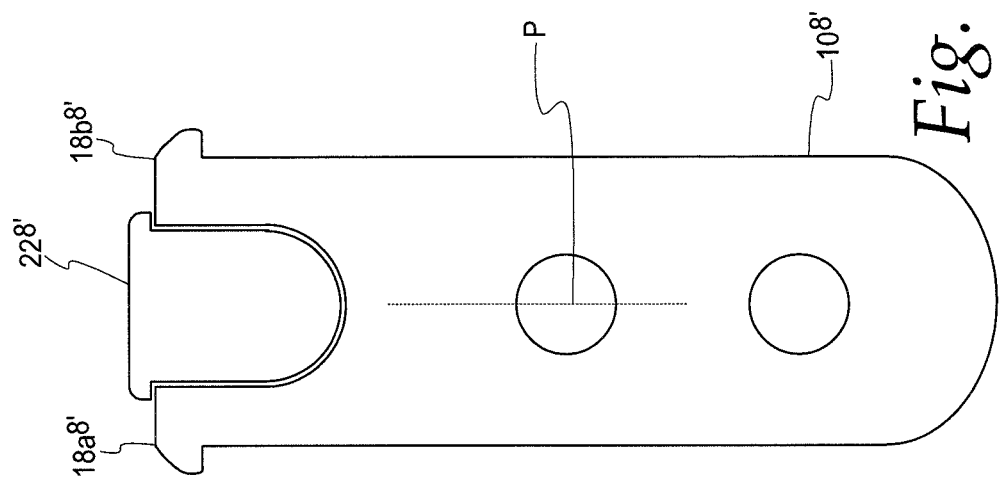
FIG. 26 is a schematic representation of an implant operatively positioned with a guide assembly and with a further modified form of cooperating rail and slot arrangement.

In FIG. 26, another form of implant is shown schematically at $10^{7'}$, with projections $18a^{7'}$, $18b^{7'}$, operatively positioned with respect to part of a guide assembly $22^{7'}$. The implant $10^{7'}$ and guide assembly $22^{7'}$ have a modified cooperating rail and slot arrangement.

Figure 27:
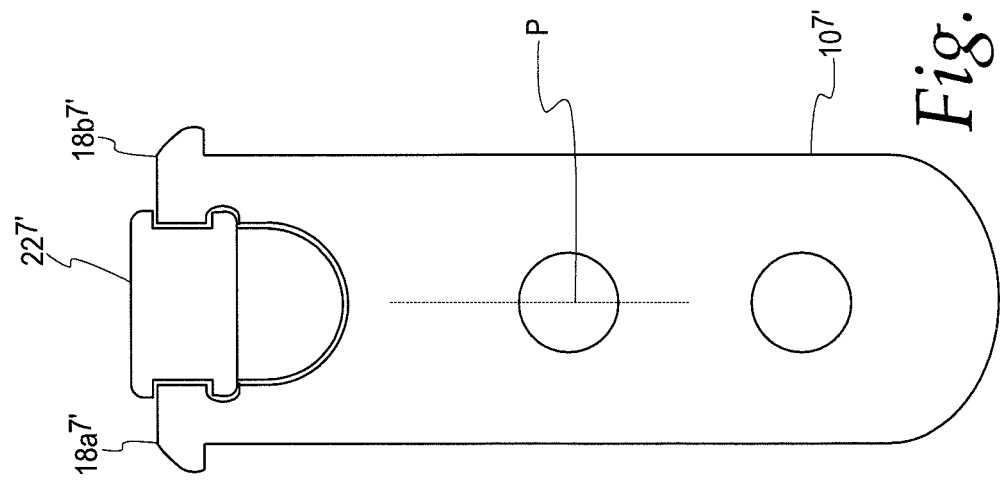
FIG. 27 is a schematic representation as in FIG. 26 and showing a further modified form of cooperating rail and slot arrangement.

In FIG. 27, a further form of implant is shown schematically at $10^{8'}$, with projections $18a^{8'}$, $18b^{8'}$, operatively positioned with respect to a part of a guide assembly $22^{8'}$. A further modified cooperating rail and slot arrangement is depicted.

While the projections described above are substantially straight, the projections might have a bent or formed shape that is not precisely straight. The same structures described above can be used to stabilize and guide these projections in substantially the same manner. As but one example, each non-straight projection might contact a respective guide assembly at spaced locations and still be stabilized and guided by the guide assembly surfaces.

The bone implant handling assembly 12 and a plurality of different bone implants can be offered as a kit whereby a surgeon can select and use the different bone implants interchangeably, one in place of the other depending upon the desired form of the implant and/or its adaptability to different bones and sites.

In the FIGS. 26 and 27 structures, there are complementary/reciprocal slot and rail arrangements on each side of the aforementioned reference plane P. That is, on each side of the plane, each of the implants and guide assemblies effectively has both a slot and rail that cooperates with a rail and slot on the other of the implants and guide assemblies.

With these designs, and those previously described, there are several guiding surfaces on the relatively moving components that interact at different locations and in different relationships and orientations that contribute to consistent and stable relative movement that ultimately allows the particular implant to maintain orientation and be placed precisely where desired.

Figure 28:
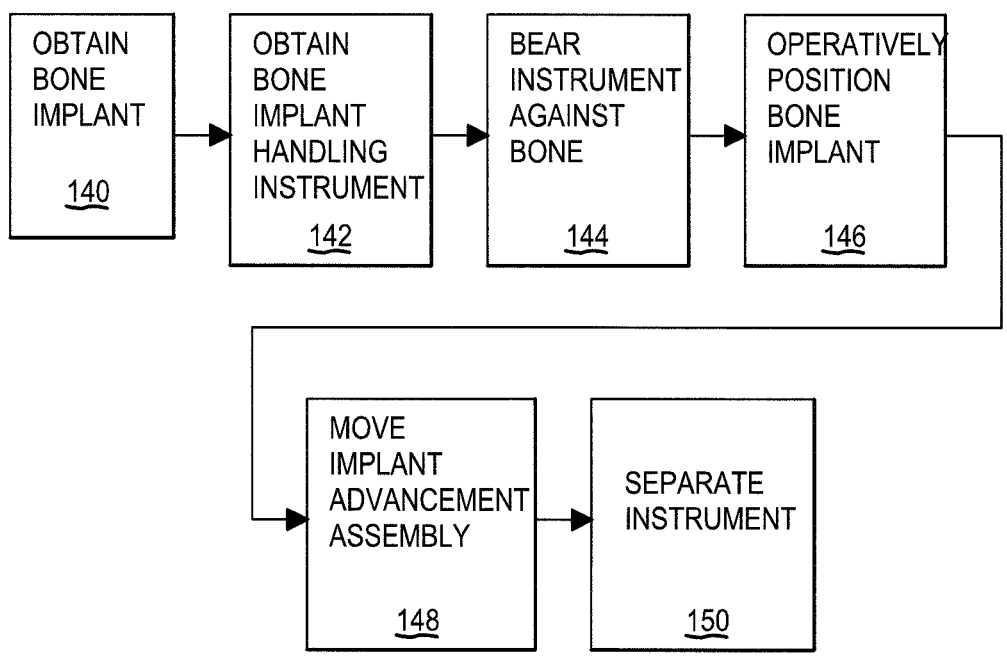
FIG. 28 is a flow diagram representation of a method of placing a bone implant in an operative position with respect to at least one bone part, according to the invention.

With the above structures, a method of placing a bone implant in an operative position with respect to at least one bone part can be carried out as shown in flow diagram form in FIG. 28.

As shown at block 140, a bone implant having a body with a first portion and first and second projections is obtained.

As shown at block 142, a bone implant handling instrument, having a guide assembly and an implant advancing assembly, is obtained.

As shown at block 144, a part of the bone implant handling instrument is borne against at least one bone part at a first location. As noted above, this step may take place as part of different optional sequences.

As shown at block 146, the bone implant is operatively positioned with respect to the guide assembly.

As shown at block 148, with the part of the bone implant handling instrument bearing against the at least one bone part at the first location and the bone implant operatively positioned, a part of the implant advancing assembly is moved guidingly relative to the guide assembly to cause the part of the implant advancing assembly to advance the bone implant in a straight line, generally towards the first location, while causing the bone implant and bone implant handling instrument to cooperate to maintain the bone implant in a same orientation relative to the straight line, into an operative position wherein the first and second projections are advanced into one or more bone parts and the first portion of the body overlies an external bone surface.

As shown at block 150, as an incident of the bone implant realizing the operative position, the bone implant and bone implant handling instrument are caused to assume a relationship wherein the bone implant handling instrument can be separated, and moved away, from the bone implant.

Preparatory to directing the projections into bone, the bone might be pre-drilled to accept the free ends of the projections.

The above embodiment of the instrument 12 lends itself to being readily assembled and disassembled, which may facilitate manufacture and facilitates cleaning.

The design can be such that the implant, initially in a fully separated state, can be operatively positioned through a relatively simple movement of the implant relative to the instrument.

At the same time, since the instrument can be designed so that fasteners do not have to be used to connect or disconnect the implant, a simplified procedure is made possible, representing a convenience that may shorten overall procedure time and reduce user fatigue.

As explained above, the basic design is adaptable to multiple different types of implants used for different applications and at different locations.

The foregoing disclosure of specific embodiments is intended to be illustrative of the broad concepts comprehended by the invention.

The invention claimed is:

1. In combination:
    a) a first bone implant comprising a body with a first portion configured to overlie an outer bone surface with the first bone implant in an operative position and first and second projections each configured to extend into at least one bone part with the first bone implant in the operative position,
    the first and second projections respectively having first and second free ends; and
    b) a bone implant handling instrument comprising:
    a guide assembly; and
    an implant advancing assembly,
    the guide assembly first bone implant, and a part of the bone implant handling instrument configured so that with the part of the bone implant handling instrument bearing against at least one bone part at a first location and the first bone implant operatively positioned with respect to the guide assembly the first bone implant can be guided in substantially a straight line in a first direction, generally toward the first location, while being maintained in substantially a same orientation with respect to the straight line between a starting position and the operative position,
    the implant advancing assembly comprising at least one part that is configured to be movable against the first bone implant to thereby drive the first bone implant from the starting position into the operative position the first bone implant further configured so that with the first and second projections advanced into one or more bone parts the first portion of the body overlies an outer bone surface,
    the bone implant handling instrument and the first bone implant configured so that as an incident of the first bone implant being moved into the operative position the bone implant handling instrument and first bone implant are in a relationship wherein the bone implant handling instrument can be moved away from the bone implant.

2. The combination according to claim 1 wherein the at least one part is movable guidingly on the bone implant handling instrument.

3. The combination according to claim 1 wherein the first bone implant and guide assembly define a cooperating rail and slot arrangement that guides the first bone implant in the straight line.

4. The combination according to claim 3 wherein the implant handling instrument has a central longitudinal axis substantially aligned with the straight line, the rail and slot arrangement comprises a rail on the guide assembly with spaced ends and the rail on the guide assembly has a discrete gap between the spaced ends that permits a part of the first bone implant to be advanced radially through the discrete gap to facilitate operative positioning of the first bone implant relative to the guide assembly.

5. The combination according to claim 3 wherein the first and second projections make up a part of the rail and slot arrangement and are respectively guided in first and second slots on the guide assembly and cooperate to block reorientation of the first bone implant with respect to the straight line with the bone implant moving in the straight line.

6. The combination according to claim 1 wherein the guide assembly and implant advancing assembly define a cooperating rail and slot arrangement that is configured to cause the at least one part to be guided in a controlled path up to and against the operatively positioned first bone implant.

7. The combination according to claim 6 wherein the first bone implant and guide assembly define another cooperating rail and slot arrangement that guides the first bone implant in the straight line and one rail defines a part of each of the cooperating rail and slot arrangements.

8. The combination according to claim 1 wherein the bone implant handling instrument has a central longitudinal axis substantially aligned with the straight line.

9. The combination according to claim 8 wherein the first bone implant and guide assembly define first and second cooperating rail and slot arrangements on opposite sides of a plane containing the longitudinal axis that guide the first bone implant in the straight line and that act to block reorientation of the first bone implant with respect to the straight line with the first bone implant moving in the straight line.

10. The combination according to claim 9 wherein the first and second cooperating rail and slot arrangements comprise first and second slots on the guide assembly that open away from each other and first and second rails on the first bone implant that reside respectively in the first and second slots with the first bone implant operatively positioned with respect to the guide assembly.

11. The combination according to claim 9 wherein the first cooperating rail and slot arrangement comprises a rail and slot on the guide assembly that respectively cooperate with a slot and rail on the first bone implant.

12. The combination according to claim 8 wherein the guide assembly has an axially extending bore and further in combination with a locating wire that is extendable into bone and slidable guidingly within the axially extending bore to facilitate placement of the bone implement handling instrument with respect to one or more bone parts preparatory to operatively positioning the first bone implant.

13. The combination according to claim 1 wherein the first bone implant and guide assembly are configured so that with the first bone implant operatively positioned with respect to the guide assembly, the first bone implant is releasably frictionally maintained in relationship to the guide assembly whereupon a force must be applied by a user to the first bone implant to move the first bone implant relative to the guide assembly in the straight line.

14. The combination according to claim 1 wherein the implant advancing assembly comprises an enlarged graspable head that moves as one piece with the at least one part of the implant advancing assembly, whereby a user can manipulate the enlarged graspable head to drive the first bone implant from the starting position into the operative position.

15. The combination according to claim 1 wherein the implant advancing assembly comprises a substantially flat impact surface that moves as one piece with the at least one part of the implant advancing assembly, whereby a user can strike the impact surface to generate a force that is at an angle to a plane of the impact surface to thereby drive the first bone implant towards the operative position.

16. The combination according to claim 1 wherein the part of the bone implant handling system that can be borne against at least one bone part at the first location comprises a plurality of feet each with a sharp tip configured to bear against at least one bone part at the first location.

17. The combination according to claim 1 wherein the first and second projections have first and second substantially parallel lengths.

18. The combination according to claim 17 wherein the first portion of the body is a formed plate.

19. The combination according to claim 17 wherein the first portion of the body comprises a formed wire shape.

20. The combination according to claim 17 wherein the first portion of the body comprises a formed wire shape and at least one plate fixed to the formed wire shape.

21. The combination according to claim 14 wherein the first and second projections have facing substantially parallel surfaces that act against the guide assembly to guide movement of the first bone implant in the straight line and block reorientation of the first bone implant with respect to the straight line with the first bone implant moving in the straight line.

22. The combination according to claim 21 wherein the guide assembly has substantially parallel surfaces that face away from each other, are substantially parallel to the facing substantially parallel surfaces, and cooperate one each with the facing substantially parallel surfaces to guide movement of the first bone implant in the straight line and block reorientation of the first bone implant with respect to the straight line with the first bone implant moving in the straight line.

23. The combination according to claim 1 wherein the first bone implant has facing surface regions between which a portion of the guide assembly resides, the facing surface regions and the portion of the guide assembly cooperating to block reorientation of the first bone implant with respect to the straight line with the first bone implant moving in the straight line.

24. The combination according to claim 1 wherein the first bone implant has a convex "U" shape at first and second locations respectively where the first and second projections connect to the first portion of the body and the at least one part on the implant advancing assembly is movable against the convex U shapes at each of the first and second locations in driving the first bone implant into the operative position.

25. The combination according to claim 24 wherein the at least one part comprises first and second discrete concave surfaces that bear one each against the convex U shapes.

26. The combination according to claim 1 wherein the guide assembly has a contoured outside surface configured to accept a user's fingers to facilitate grasping of the guide assembly.

27. The combination according to claim 1 wherein the first bone implant is in the form of a hook plate.

28. The combination according to claim 1 wherein the first bone implant is in the form of a staple.

29. The combination according to claim 1 wherein there is at least one detent component on each of the guide assembly and implant advancing assembly that cooperate to releasably consistently maintain the guide assembly and implant advancing assembly in first and second different predetermined relationships.

30. The combination according to claim 1 further in combination with at least a second bone implant having a different configuration than the first bone implant, the at least second bone implant comprising a body with a first portion configured to overlie an outer bone surface with the at least second bone implant in an operative position and first and second projections each configured to extend into at least one bone part with the at least second bone implant in its operative position, the at least second bone implant and bone implant handling instrument configured so that the at least second bone implant can be used in place of the first bone implant to cooperate with the bone implant handling instrument in substantially a same manner as the first bone implant cooperates with the bone implant handling instrument so that with the second bone implant operatively positioned with respect to the guide assembly the bone implant handling instrument can be used to advance the second bone implant between a respective starting position and a respective operative position.

31. The combination according to claim 30 wherein the first bone implant and at least second bone implant are configured to cooperate with different bones.

32. The combination according to claim 30 wherein the first bone implant and at least second bone implant are configured to cooperate with a same bone.

* * * * *

UNITED STATES PATENT AND TRADEMARK OFFICE
CERTIFICATE OF CORRECTION

PATENT NO. : 12,213,712 B2
APPLICATION NO. : 17/738536
DATED : February 4, 2025
INVENTOR(S) : Lukas Tellman Page 1 of 1

It is certified that error appears in the above-identified patent and that said Letters Patent is hereby corrected as shown below:

In the Claims

Column 15, Line 8, should read as follows:
1. In combination:
a) a first bone implant comprising a body with a first portion configured to overlie an outer bone surface with the first bone implant in an operative position and first and second projections each configured to extend into at least one bone part with the first bone implant in the operative position,
the first and second projections respectively having first and second free ends; and
b) a bone implant handling instrument comprising:
a guide assembly; and
an implant advancing assembly,
the guide assembly, first bone implant, and a part of the bone implant handling instrument configured so that with the part of the bone implant handling instrument bearing against at least one bone part at a first location and the first bone implant operatively positioned with respect to the guide assembly, the first bone implant can be guided in substantially a straight line in a first direction, generally toward the first location, while being maintained in substantially a same orientation with respect to the straight line between a starting position and the operative position,
the implant advancing assembly comprising at least one part that is configured to be movable against the first bone implant to thereby drive the first bone implant from the starting position into the operative position, the first bone implant further configured so that with the first and second projections advanced into one or more bone parts, the first portion of the body overlies an outer bone surface,
the bone implant handling instrument and the first bone implant configured so that as an incident of the first bone implant being moved into the operative position the bone implant handling instrument and first bone implant are in a relationship wherein the bone implant handling instrument can be moved away from the bone implant.

Signed and Sealed this
Sixth Day of May, 2025

Coke Morgan Stewart
*Acting Director of the United States Patent and Trademark Office*